(12) United States Patent
Ju et al.

(10) Patent No.: US 8,784,551 B2
(45) Date of Patent: Jul. 22, 2014

(54) BONE CEMENT FORMULA AND BIORESORBABLE HARDENED BONE CEMENT COMPOSITES PREPARED WITH THE SAME

(75) Inventors: Chien-Ping Ju, Kansas, MO (US); Jiin-Huey Chern Lin, Winnetka, IL (US)

(73) Assignee: National Cheng Kung University, Tainan (TW)

( * ) Notice: Subject to any disclaimer, the term of this patent is extended or adjusted under 35 U.S.C. 154(b) by 818 days.

(21) Appl. No.: 12/907,091

(22) Filed: Oct. 19, 2010

(65) Prior Publication Data

US 2012/0095518 A1 Apr. 19, 2012

(51) Int. Cl.
| | | |
|---|---|---|
| C04B 11/00 | (2006.01) |
| C04B 41/50 | (2006.01) |
| A61L 24/00 | (2006.01) |
| A61L 27/46 | (2006.01) |
| C04B 28/34 | (2006.01) |
| C04B 41/00 | (2006.01) |
| C04B 111/00 | (2006.01) |

(52) U.S. Cl.
CPC .......... C04B 28/34 (2013.01); C04B 41/5092 (2013.01); *A61L 2430/02* (2013.01); *A61L 24/0063* (2013.01); *A61L 27/46* (2013.01); *C04B 2111/00836* (2013.01); *C04B 41/009* (2013.01); *C04B 28/346* (2013.01)

USPC ............ 106/35; 106/690; 106/691; 106/772; 106/778

(58) Field of Classification Search
CPC .... C04B 11/00; C04B 11/002; C04B 12/025; C04B 12/027; C04B 22/143; C04B 22/16; C04B 24/06; C04B 38/02
USPC ........................... 106/35, 690, 691, 772, 778
See application file for complete search history.

(56) References Cited

U.S. PATENT DOCUMENTS 7,670,419 B2 * 3/2010 Bohner ........................ 106/35

* cited by examiner

*Primary Examiner* — Paul Marcantoni
(74) *Attorney, Agent, or Firm* — Bacon & Thomas, PLLC

(57) ABSTRACT

The present invention provides a bone cement formula having a powder component and a setting liquid component, wherein the powder component includes a calcium sulfate source and a calcium phosphate source with a weight ratio of the calcium sulfate source less than 65%, based on the total weight of the calcium sulfate source and the calcium phosphate source, and the setting liquid component comprises ammonium ion ($NH_4^+$) in a concentration of about 0.5 M to 4 M, wherein the calcium phosphate source includes tetracalcium phosphate (TTCP) and dicalcium phosphate in a molar ratio of TTCP to dicalcium phosphate of about 0.5 to about 2.5, and the calcium sulfate source is calcium sulfate hemihydrate (CSH), calcium sulfate dehydrate (CSD), or anhydrous calcium sulfate.

44 Claims, No Drawings

BONE CEMENT FORMULA AND BIORESORBABLE HARDENED BONE CEMENT COMPOSITES PREPARED WITH THE SAME

FIELD

The exemplary embodiment(s) of the present invention relates to bone repairing substance for medicaments. More specifically, the exemplary embodiment(s) of the present invention relates to a bone cement formula.

BACKGROUND

Bone cement compositions are widely used in bonding, filling, and/or repairing damaged natural bone. Bone cement is typically used in orthopedic, dental procedures, and/or other medicinal applications. Despite many advantages such as excellent biocompatibility, superior osteoconductivity, and enhanced mechanical or physical strength, the majority of calcium phosphates exhibit clinically low bioresorption rates. On the other hand, the compound of calcium sulfates also illustrate higher dissolution rates, which, for many applications, is typically too high of dissolution rate for allowing new bone cells to quickly grow in a bone cavity. The composite including calcium sulfates generally has lower mechanical and/or physical strengths than calcium phosphates.

Another problem associated with conventional bone cement paste is prolong setting time whereby it hampers applicability to various applications. For example, calcium phosphate (CPC) paste, which is described in U.S. Pat. No. 4,612,053, typically requires prolong setting time.

SUMMARY

Embodiment(s) of the present invention discloses a method of providing a calcium phosphate-calcium sulfate composite that exhibits enhanced strength, excellent biocompatibility, superior osteoconductivity, appropriate and adjustable bioresorption rate.

The objectives of embodiments are to provide a bone cement formula, a bone cement paste, a hardened bone cement composite from paste, a hardened bone cement composite with enhanced strength by pressurizing the paste while leaking solution from the paste, and porous hardened bone cement composite from the paste.

The embodiments of the present invention provides methods for providing a bone cement formula, bone cement paste, hardened bone cement composite, hardened bone cement composite with enhanced strength, and porous hardened bone cement composite.

An embodiment of the present invention provides a method for filling a hole or cavity in a bone with an exemplary embodiment of bone cement paste which will cure or harden in a hole or cavity in need of treatment. Another embodiment of the present invention provides a method for implanting hardened bone cement composite during a treatment.

Preferably, said treatment is an orthopedic treatment or a dental treatment, and said hardened bone cement composite is implanted in a bone of a subject.

Preferably, said implanting comprises breaking up said hardened bone cement composite into pellets and filling a hole or cavity in a bone of a subject with said pellets.

Preferably, the method of treatment further comprises mixing a pore-forming agent with the powder component or with the paste; shaping the paste in a mold; removing the mold to form a block of hardened bone cement composite with the pore-forming agent embedded therein; and immersing said block of hardened bone cement composite with the pore-forming agent embedded therein in an immersing liquid to dissolve said pore-forming agent in the immersing liquid, creating pores therein, so that a porous block is formed, and thus said implanting comprises implanting said porous block in said subject in need of said treatment.

Preferably, said implanting comprises breaking up the porous block into pellets and filling a hole or cavity in a bone of said subject with said pellets.

One embodiment of the present invention provides a bone cement formula which includes a powder component and a setting liquid component with a liquid to powder ratio of 0.20 cc/g to 0.50 cc/g (cc is cubic centimeter, g is gram), preferably 0.25 cc/g to 0.35 cc/g. The powder component, in one aspect, includes a calcium sulfate source and a calcium phosphate source with a weight ratio of the calcium sulfate source less than 65%, based on the total weight of the calcium sulfate source and the calcium phosphate source. The setting liquid component, in one aspect, includes ammonium ion ($NH_4^+$) in a concentration of about 0.5 M to 4 M. The calcium phosphate source, in one aspect, includes tetracalcium phosphate (TTCP) and dicalcium phosphate in a molar ratio of TTCP to dicalcium phosphate of about 0.5 to about 2.5, preferably about 1.0, and the calcium sulfate source is calcium sulfate hemihydrate (CSH), calcium sulfate dehydrate (CSD), or anhydrous calcium sulfate, and preferably, CSH.

It should be noted that, for different medical indications, the required resorption rates can be different. As such, more desirable cement should be able to provide a range of bone resorption rates without substantially changing its primary formula, performance and working/setting times. For example, a resorption rate of implanted hardened cement composite can be adjustable due to co-existence of a calcium sulfate source and a calcium phosphate source. Our animal study demonstrates that the resorption rate of our hardened sulfate-phosphate cement composite can be adjusted by adjusting the sulfate/phosphate ratio.

In one embodiment, calcium sulfate source of the powder component is greater than 5%, and preferably in a range of 10% to 55%, based on the total weight of the calcium sulfate source and the calcium phosphate source powder. Calcium phosphate source, in one aspect, includes tetracalcium phosphate (TTCP) and dicalcium phosphate, preferably DCPA, in a molar ratio of TTCP to dicalcium phosphate of approximately 0.5 to 2.5, preferably about 1.0, and the calcium sulfate source is calcium sulfate hemihydrate (CSH), calcium sulfate dehydrate (CSD), or anhydrous calcium sulfate, and preferably, CSH.

As illustrated or demonstrated in Control Examples 1-4, detailed discussion in the section of Experiential Procedures below, the combination of TTCP, DCPA and CSH is essential. As TTCP, DCPA, and CSH can be combined or mixed in a certain weight-ratio range, various unique and non-replaceable results are obtained. On the other hand, various experiments of mixtures of two compounds, such as TTCP/CSH and DCPA/CSH, result unsatisfactory results.

Although ammonium is generally considered as a rather toxic component, the experiment, shown below, illustrates that ammonium provides not only a cytotoxically acceptable cement formula, but also a cement formula with unprecedented performance. When concentration of ammonium ions is too low, the cement paste can be either dispersed right upon contact with liquid, such as water or body fluid (i.e., blood), or has an initial mechanical strength that is too low to maintain cement paste integrity which can cause premature fracture of cement paste. On the other hand, when ammonium ion concentration is too high, the cement paste becomes too toxic to be used as an implant.

In one embodiment, the setting liquid component comprises ammonium ion ($NH_4^+$) in a concentration of about 1.0 M to 2.0 M, and more preferably about 1.2 M.

The setting liquid component, in one example, is a solution of $NH_4H_2PO_4$, $(NH_4)_2HPO_4$, $(NH_4)_3PO_4 \cdot 3H_2O$ or a mixture of them. Preferably, the setting liquid component is an aqueous solution. Selectively, the setting liquid component further comprises citric acid or tartaric acid dissolved therein. The setting liquid component preferably has a pH of about 7.0 to about 9.0.

In one embodiment, the powder component comprises a pore-forming agent which is to be dissolved in a solution when hardened bone cement composite is immersed in the solution. Preferably, the pore-forming agent is selected from the group consisting of LiCl, KCl, NaCl, $MgCl_2$, $CaCl_2$, $NaIO_3$, KI, $Na_3PO_4$, $K_3PO_4$, $Na_2CO_3$, amino acid-sodium salt, amino acid-potassium salt, glucose, polysaccharide, fatty acid-sodium salt, fatty acid-potassium salt, potassium bitartrate ($KHC_4H_4O_6$), potassium carbonate, potassium gluconate ($KC_6H_{11}O_7$), potassium-sodium tartrate ($KNaC_4H_4O_6 \cdot 4H_2O$), potassium sulfate ($K_2SO_4$), sodium sulfate, sodium lactate and mannitol. The amount of the pore-forming agent used is proportional to the porosity of the hardened bone cement composite to be achieved.

In one embodiment, the calcium phosphate source is a mixture of TTCP and DCPA. The bone cement formula, in one aspect, allows bone cement paste having a desirable working time and a setting time, so that the operator has a sufficient period of time to fill the hole or cavity with the paste before the paste becomes hardened. It should be noted that filled paste will develop minimum strength required by the treatment within an acceptable short period of time.

The hardened bone cement composite, in one embodiment, possesses a low toxicity whereby it is safe to be applied to a patient, for example. Note that hardened bone cement has a characteristic of high initial strength with an improved bioresorbable rate.

Additional features and benefits of the present invention will become apparent from the detailed description, figures and claims set forth below.

DETAILED DESCRIPTION

Embodiments of the present invention are described herein in the context of method, formula, system, and/or process for preparing a hardened bone cement composite having an enhanced bioresorbable rate for medicaments. Those of ordinary skills in the art will realize that the following detailed description of the embodiment(s) is illustrative only and is not intended to be in any way limiting. Other embodiments of the present invention will readily suggest themselves to such skilled persons having the benefit of this disclosure.

References to "one embodiment," "an embodiment," "example embodiment," "various embodiments," "exemplary embodiment," "one aspect," "an aspect," "exemplary aspect," "various aspects," etc., indicate that the embodiment(s) of the invention so described may include a particular feature, structure, or characteristic, but not every embodiment necessarily includes the particular feature, structure, or characteristic. Further, repeated use of the phrase "in one embodiment" does not necessarily refer to the same embodiment, although it may.

In the interest of clarity, not all of the routine features of the implementations and/or processes described herein are shown and described. It will, of course, be appreciated that in the development of any such actual implementation, numerous implementation-specific decisions will be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking for those of ordinary skills in the art having the benefit of this disclosure.

Embodiment(s) of the present invention is bioresorbable bone cement applicable to various medical fields, such as orthopedic, spinal, and dental surgeries. Characteristics or properties of the bioresorbable bone cement or formula have convenient working environment(s) and setting times to form a hardened block with high strength, excellent biocompatibility and superior osteoconductivity, and adjustable (or flexible) bioresorption rate.

To prepare or make the bioresorbable bone cement having properties of flexible (or convenient) work environment (or time) and setting times to form hardened bone cement composites with desirable strength and biological compatibility, one embodiment of the present invention discloses a bone cement formula which is be described more details below. In one aspect, a method or process for preparing hardened bone cement composite involves producing bone cement paste and placing the paste in an environment where the paste can set.

A process for preparing bone cement paste, in one embodiment, comprises mixing powder component with setting liquid component by a mixing mechanism such as agitation. The powder component, for example, may include mixture of calcium sulfate source and calcium phosphate source. Alternatively, calcium sulfate source and calcium phosphate source can be separate powders. In this case, calcium sulfate source and calcium phosphate source are combined first to form a power mixture prior to mixing with setting liquid component.

The calcium sulfate source and calcium phosphate source discussed earlier can be tetracalcium phosphate (TTCP) and/or dicalcium phosphate anhydrous (DCPA) powders. It should be noted that other types of sources can be used as long as they have similar chemical properties or characteristics as TTCP and/or DCPA.

The bone cement paste, in one embodiment, becomes hard or cured within a period of setting time under an atmosphere environment or an environment surrounded by body fluid such as blood. During an operation, an operator or doctor places bone cement paste into a hole or cavity at a damaged bone via a suitable tool through an incision. For example, for an orthopedic, spinal or root canal treatment, when bone cement paste becomes or cures into hardened bone cement composite in-situ, the hardened bone cement will be resorbed by the subject body over time in accordance with a predefined bioresorption rate. Depending on applications, bone cement paste, in one embodiment, can be shaped into a rigid or semi-rigid block of bone cement composite before it is implanted in the subject body to repair damaged parts such as bones or teeth.

The bone cement paste, in one embodiment, can be injected into a bone hole or cavity with an orthopedic paste delivering tool such as a conventional medical instrument described in U.S. Pat. No. 7,325,702 B2 or shaped through a mold, in which the paste will form a block of hardened bone cement composite. It should be noted that an orthopedic delivering tool is able to continually deliver the paste into a bone cavity until the cavity is filled.

Depending on applications, a dense block of cement can be formed if the powder component does not contain the appropriate pore-forming agents. The dense block, for example, can be formed by pressurizing the bone cement paste in a mold before the paste sets in order to drain or remove a portion of liquid from the paste whereby a liquid/powder ratio of the paste decreases. In one aspect, the pressure applied to the paste at the mold has a range from approximately 1 megapascal ("MPa") to 500 MPa, preferably from 100 MPa to 500 MPa. It is noted that the dense block has a superior compressive strength which can be used as a medical implant. It should be further noted that a rigid or solid dense block of calcium phosphate cement is impregnated with an impregnating liquid for a predefined period of time, so that overall compressive strength of the resulting impregnated block is increased compared to a block which has not undergone such impregnating treatment. The impregnating liquid, in one embodiment, is phosphate-containing solution. Exemplary aqueous solution may include, but not limited to, $(NH_4)_3PO_4$, $(NH_4)_2HPO_4$, $NH_4H_2PO_4$, $K_3PO_4$, $K_2HPO_4$, $KH_2PO_4$, $Na_3PO_4$, $Na_2HPO_4$, $NaH_2PO_4$, or $H_3PO_4$. The phosphate-containing solution, in one example, has a phosphate concentration of about 0.1 M to about 6 M, preferably from about 1 M to about 3 M.

A porous block can be utilized as a tissue-engineered scaffold when the powder component of the bone cement formula contains pore-forming agent. The pore-forming agent can be removed from a molded block by immersing the molded block in immersing liquid so that the pore-forming agent is dissolved in the immersing liquid. The pore-forming agent may be added during the mixing of the powder component and the setting liquid component, or may be added to the resultant paste before it is placed in a mold. The immersing liquid, for example, can be an acidic aqueous solution, a basic aqueous solution, a physiological solution, an organic solvent or substantially pure water. In one embodiment, the immersing liquid is the same as the above-mentioned impregnating liquid. In one embodiment, the immersing liquid is waster. In one aspect, the porous block has a porosity of 50-90 vol %. The dense block or porous block prepared in accordance with the bone cement formula, in one embodiment, can be deposited within living cells, a growth factor and/or a drug by impregnating the block in a suspension of living cells or a solution of the growth factor and/or drug.

The following examples via experimental procedures are illustrative and are intended to demonstrate embodiments of the present invention, which, however, should not be taken to limit the embodiments of the invention to the specific embodiments, but are for explanation and understanding only, since numerous modifications and variations will be apparent to those skilled persons in this art.

| Experimental procedures Abbreviation | |
|---|---|
| TTCP | tetracalcium phosphate |
| DCPA | dicalcium phosphate anhydrous |
| CSH | calcium sulfate hemihydrate |
| WT | Working time |
| ST | Setting time |
| L/P ratio | Liquid/powder ratio |
| CS | Compressive strength |

Symbols Used in Tables
: Paste cannot be formed by mixing powder and liquid for 2 minutes.
*: After being removed from the mold (30 minutes from mixing powder and liquid), the hardened cement blocks collapses and disintegrates into powder form when it is immersed in Hanks' solution for 1 day.
X: Hardened cement blocks are broken (fractured/cracked but not dispersed into powder form) after being immersed in Hanks' solution for 1 day.

Preparation of TTCP Powder

The TTCP powder was fabricated in-house from the reaction of dicalcium pyrophosphate ($Ca_2P_2O_7$) (Sigma Chem. Co., St. Louis, Mo., USA) and calcium carbonate ($CaCO_3$) (Katayama Chem. Co., Tokyo, Japan) using the method suggested by Brown and Epstein [Journal of Research of the National Bureau of Standards—A Physics and Chemistry 6 (1965) 69A 12].

TTCP powder was prepared by mixing $Ca_2P_2O_7$ powder with $CaCO_3$ powder uniformly for 12 hours. The mixing ratio of $Ca_2P_2O_7$ powder to $CaCO_3$ powder was 1:1.27 (weight ratio) and the powder mixture was heated to 1400° C. to allow two powders to react to form TTCP.

Preparation of a TTCP/DCPA/CSH Composite Paste

Appropriate amounts of TTCP and DCPA powders were uniformly mixed in a ball miller, followed by uniformly mixing with appropriate amount of CSH powder. The resultant TTCP/DCPA/CSH mixed powders were mixed uniformly with a desirable setting solution (e.g., 0.6M $(NH_4)_2HPO_4$) at a desirable L/P ratio (e.g., 0.28 cc/g) to form a TTCP/DCPA/CSH paste.

Chemicals Used for the Study

| Chemical | Formula | Manufacturer | Location |
|---|---|---|---|
| Tetracalcium phosphate (TTCP) | $Ca_4(PO_4)_2O$ | Fabricated in-house | Taiwan |
| Dicalcium phosphate anhydrous (DCPA) | $CaHPO_4$ | ACROS | New jersey, USA |
| Calcium sulfate hemihydrate (CSH) | $CaSO_4 \cdot \frac{1}{2}H_2O$ | Showa | Tokyo, Japan |
| Diammonium hydrogen phosphate | $(NH_4)_2HPO_4$ | Showa | Tokyo, Japan |
| Diammonium dihydrogen phosphate | $NH_4H_2PO_4$ | Showa | Tokyo, Japan |
| Dipotassium hydrogen phosphate | $K_2HPO_4$ | Showa | Tokyo, Japan |
| Tartaric acid | $C_2H_2(OH)_2(COOH)_2$ | Katayama | Osaka, Japan |
| Citric acid | $C_6H_8O_7$ | Pantreac | Barcelona, Spain |
| Malic acid | $C_2H_3(OH)(COOH)_2$ | Pantreac | Barcelona, Spain |

Compressive Strength Testing of Composite Cement

To measure the CS of a hardened cement, after mixing for 1 min, the cement paste was packed in a 6 mm diameter, 12 mm deep cylindrical stainless steel mold under a pressure of 1.4 MPa for 30 min. After being removed from the mold, the hardened cement samples were immersed in Hanks' physiological solution which was maintained at 37° C. and agitated daily to help maintain uniform ion concentrations. After immersion, samples were removed from the solution for CS testing while samples are still wet ("test under wet condition"). The CS testing was conducted using a desk-top mechanical tester (Shimadzu AG-10kNX, Tokyo, Japan) at a crosshead speed of 1.0 mm/min. The test method is according to ASTM 451-99a method.

Working Time/Setting Time Measurement

The working time of cement paste was determined by the time after that the cement paste was no longer workable. The setting time of cement paste was measured according to the standard method set forth in ISO 1566 for dental zinc phosphate cements. The cement is considered set when a 400 gm weight loaded onto a Vicat needle with a 1 mm diameter tip fails to make a perceptible circular indentation on the surface of the cement.

pH Measurement

The early stage (during setting process) variation in pH was determined using a pH meter (Suntex Instruments SP2000, Taipei, Taiwan) that was buried in the cement paste immediately after the powder and setting liquid were mixed. The first reading was taken at 1 minute after mixing. The measurement was continued until the paste nearly becomes set. Readings were taken every 30 seconds until 30 minutes after mixing. After then they were taken every 60 seconds.

The variation in pH value of Hanks' solution in which the cement paste sample was immersed was monitored using the same pH meter. 2 g cement paste was taken after mixing the powder and the setting solution for 5 minutes, and it was immersed in 20 ml Hanks' solution with a pH value of 7.05 for the test. The solution was maintained at 37° C. throughout testing and continually stirred to help maintain uniform ion concentrations of the solution.

Cytotoxicity Test

The cytotoxicity test was performed according to ISO 10993-5. The extraction method was used. NIH/3T3 fibroblasts (seeding density 5000 per well) were pre-cultured for 24 h in Dulbecco's modified essential medium (DMEM) supplemented with bovine serum (10%) and PSF (1%). An extract was prepared by immersing a hardened cement paste in the culture medium at a ratio of 0.1 (g/ml) at 37° C. for 24 h and then collecting the liquid by centrifugation. The extract was added to the 96 well microplate (100 μl per well) incubated in a 5% $CO_2$ humidified atmosphere at 37° C. After 24 h, the extract was sucked out and then a mixture of the culture medium (100 μl) and WST-1 (10 μl) was added to the wells and incubated for 1 h at 37° C. Cell viability was measured by using the WST-1 assay. This is a colorimetric assay of mitochondrial dehydrogenase activity where the absorbance at 450 nm is proportional to the amount of dehydrogenase activity in the cell. After 1 h incubation, the mixture of medium and WST-1 was transferred to a 96 well microplate and the absorbance at 450 nm was measured with an ELISA reader. $Al_2O_3$ powder was also assayed as a control. Four bars were tested for each sample (n=4).

Cell Line Information

| Cell name | NIH/3T3 |
|---|---|
| Cell number | BCRC 60008 |
| Type | Mouse NIH/Swiss embryo |
| Growth property | Adherent, 5% $CO_2$, 37° C. |
| Morphology | Fibroblast |
| Cell culture medium | 90% Dulbecco's modified Eagle's medium (DMEM) + 10% calf serum(CS) |
| Freeze medium | 93% culture medium + 7% DMSO |

Control 1: TTCP/CSH Cement and $(NH_4)_2HPO_4$ Setting Solution

TABLE 1

TTCP/CSH mixed with 0.25-0.75M $(NH_4)_2HPO_4$

| TTCP/CSH (wt ratio) | $(NH_4)_2HPO_4$ concentration (M) | L/P ratio (cc/g) | WT (min) | ST (min) | 1 d-CS (MPa) |
|---|---|---|---|---|---|
| 90/10 | 0.25 | 0.28 | — | — | * |
|  |  | 0.33 | — | — | ✕ |
|  |  | 0.35 |  |  | ✕ |
|  | 0.50 | 0.28 | 7.4 ± 0.6 | 9.0 ± 0.7 | 3.23 ± 0.53 |
|  |  | 0.33 | 10.3 ± 0.6 | 11.6 ± 0.5 | 2.33 ± 0.56 |
|  |  | 0.35 | 11.0 ± 0.3 | 12.9 ± 0.2 | 2.40 ± 0.71 |
|  | 0.60 | 0.28 | 7.0 ± 0.3 | 8.5 ± 0.5 | 3.67 ± 0.49 |
|  |  | 0.33 | 10.1 ± 0.5 | 11.5 ± 0.6 | 3.06 ± 0.44 |
|  |  | 0.35 | 11.9 ± 0.6 | 13.0 ± 0.7 | 3.56 ± 0.74 |
|  | 0.75 | 0.28 | 5.8 ± 0.2 | 7.1 ± 0.5 | 4.07 ± 1.02 |
|  |  | 0.33 | 8.9 ± 0.1 | 11.0 ± 0.2 | 4.84 ± 0.59 |
|  |  | 0.35 | 10.4 ± 0.5 | 12.2 ± 0.2 | 3.74 ± 0.19 |
| 75/25 | 0.25 | 0.28 | — | — | * |
|  |  | 0.33 | — | — | * |
|  |  | 0.35 |  |  | * |
|  | 0.50 | 0.28 | 7.5 ± 0.3 | 10.1 ± 0.2 | 4.32 ± 0.11 |
|  |  | 0.33 | 9.7 ± 0.3 | 11.7 ± 0.3 | 7.01 ± 0.42 |
|  |  | 0.35 | 10.7 ± 0.3 | 12.5 ± 0.4 | 7.32 ± 0.38 |
|  | 0.60 | 0.28 | 6.5 ± 0.3 | 8.2 ± 0.2 | 5.92 ± 0.42 |
|  |  | 0.33 | 7.1 ± 0.3 | 9.1 ± 0.3 | 7.63 ± 0.28 |
|  |  | 0.35 | 9.0 ± 0.2 | 10.4 ± 0.1 | 8.32 ± 0.31 |
|  | 0.75 | 0.28 | 6.4 ± 0.2 | 8.0 ± 0.1 | 6.64 ± 0.52 |
|  |  | 0.33 | 7.5 ± 0.3 | 9.0 ± 0.4 | 9.55 ± 0.25 |

TABLE 1-continued

TTCP/CSH mixed with 0.25-0.75M (NH₄)₂HPO₄

| TTCP/CSH (wt ratio) | (NH₄)₂HPO₄ concentration (M) | L/P ratio (cc/g) | WT (min) | ST (min) | 1 d-CS (MPa) |
|---|---|---|---|---|---|
| 65/35 | 0.25 | 0.35 | 8.3 ± 0.3 | 9.9 ± 0.3 | 10.36 ± 0.27 |
|  |  | 0.28 | — | — | * |
|  |  | 0.33 |  |  | * |
|  |  | 0.35 |  |  | * |
|  | 0.50 | 0.28 | 7.1 ± 0.3 | 9.8 ± 0.3 | 3.37 ± 0.27 |
|  |  | 0.33 | 9.2 ± 0.2 | 11.1 ± 0.3 | 5.84 ± 0.37 |
|  |  | 0.35 | 10.5 ± 0.3 | 12.2 ± 0.4 | 6.10 ± 0.26 |
|  | 0.60 | 0.28 | 4.5 ± 0.4 | 5.3 ± 0.2 | 3.96 ± 0.12 |
|  |  | 0.33 | 7.0 ± 0.3 | 9.0 ± 0.4 | 5.44 ± 0.14 |
|  |  | 0.35 | 8.9 ± 0.4 | 9.8 ± 0.3 | 6.56 ± 0.12 |
|  | 0.75 | 0.28 | 6.3 ± 0.2 | 7.8 ± 0.2 | 4.41 ± 0.24 |
|  |  | 0.33 | 7.1 ± 0.2 | 8.4 ± 0.3 | 6.43 ± 0.27 |
|  |  | 0.35 | 8.2 ± 0.3 | 9.3 ± 0.2 | 7.55 ± 0.34 |

In the cases where the pastes were prepared with 0.25 M (NH₄)₂HPO₄ the molded lumps collapse and disintegrate when they are immersed in Hanks' solution (*), or their compressive strength cannot be measured after being immersed in Hanks' solution for 1 day (X) as shown in Table 1. As to the pastes prepared with higher concentration (NH₄)₂HPO₄ setting solutions, the hardened cement blocks give a very low compressive strength after being immersed in Hanks' solution for 1 day (1d-CS) as shown in Table 1. Apparently the powder component having only TTCP and CSH phases does not give a satisfactory result.

Control 2: TTCP/CSH Cement and NH₄H₂PO₄ Setting Solution

TABLE 2

TTCP/CSH mixed with 0.25-0.75M NH₄H₂PO₄

| TTCP/CSH (weight ratio) | NH₄H₂PO₄ concentration (M) | L/P ratio (cc/g) | WT (min) | ST (min) | 1 d-CS (MPa) |
|---|---|---|---|---|---|
| 90/10 | 0.25 | 0.28 | — | — | * |
|  |  | 0.33 | — | — | * |
|  |  | 0.35 | — | — | * |
|  | 0.50 | 0.28 | 7.4 ± 0.6 | 9.0 ± 0.7 | 3.23 ± 0.53 |
|  |  | 0.33 | 10.3 ± 0.6 | 11.6 ± 0.5 | 2.33 ± 0.56 |
|  |  | 0.35 | 11.0 ± 0.3 | 12.9 ± 0.2 | 2.40 ± 0.71 |
|  | 0.60 | 0.28 | 7.0 ± 0.3 | 8.5 ± 0.5 | 3.67 ± 0.49 |
|  |  | 0.33 | 10.1 ± 0.5 | 11.5 ± 0.6 | 3.06 ± 0.44 |
|  |  | 0.35 | 11.9 ± 0.4 | 13.0 ± 0.7 | 3.56 ± 0.74 |
|  | 0.75 | 0.28 | 5.8 ± 0.2 | 7.1 ± 0.5 | 4.07 ± 1.02 |
|  |  | 0.33 | 8.9 ± 0.1 | 11. ± 0.2 | 4.91 ± 0.66 |
|  |  | 0.35 | 10.4 ± 0.5 | 12.12 ± 0.2 | 3.74 ± 0.19 |
| 75/25 | 0.25 | 0.28 | — | — | * |
|  |  | 0.33 | — | — | * |
|  |  | 0.35 | — | — | * |
|  | 0.50 | 0.28 | — | — | * |
|  |  | 0.33 | — | — | * |
|  |  | 0.35 | — | — | * |
|  | 0.60 | 0.28 | — | — | * |
|  |  | 0.33 | — | — | * |
|  |  | 0.35 | — | — | * |
|  | 0.75 | 0.28 | — | — | * |
|  |  | 0.33 | — | — | * |
|  |  | 0.35 | — | — | * |
| 65/35 | 0.25 | 0.28 | — | — | * |
|  |  | 0.33 | — | — | * |
|  |  | 0.35 | — | — | * |
|  | 0.50 | 0.28 | — | — | * |
|  |  | 0.33 | — | — | * |
|  |  | 0.35 | — | — | * |
|  | 0.60 | 0.28 | — | — | * |
|  |  | 0.33 | — | — | * |
|  |  | 0.35 | — | — | * |
|  | 0.75 | 0.28 | — | — | * |
|  |  | 0.33 | — | — | * |
|  |  | 0.35 | — | — | * |

Table 2 shows that NH₄H₂PO₄ setting solution used in Control 2 cannot improve the (NH₄)₂HPO₄ setting solution used in Control 1 in term of the working/setting times and the 1d-CS. Apparently the powder component having only TTCP and CSH phases dose not give a satisfactory result.

Control 3: DCPA/CSH Cement and (NH₄)₂HPO₄ Setting Solution

TABLE 3

DCPA/CSH mixed with 0.25-0.75M (NH₄)₂HPO₄

| DCPA/CSH (weight ratio) | (NH₄)₂HPO₄ Concentration (M) | L/P Ratio (cc/g) | WT (min) | ST (min) | 1 d-CS (MPa) |
|---|---|---|---|---|---|
| 90/10 | 0.25 | 0.28 | — | — | * |
|  |  | 0.33 | — | — | * |
|  |  | 0.35 | — | — | * |
|  | 0.50 | 0.28 | — | — | X |
|  |  | 0.33 | — | — | X |
|  |  | 0.35 | — | — | X |
|  | 0.60 | 0.28 | — | — | X |
|  |  | 0.33 | — | — | X |
|  |  | 0.35 | — | — | X |
|  | 0.75 | 0.28 | — | — | X |
|  |  | 0.33 | — | — | X |
|  |  | 0.35 | — | — | X |
| 75/25 | 0.25 | 0.28 | — | — | X |
|  |  | 0.33 | — | — | X |

TABLE 3-continued

DCPA/CSH mixed with 0.25-0.75M $(NH_4)_2HPO_4$

| DCPA/CSH (weight ratio) | $(NH_4)_2HPO_4$ Concentration (M) | L/P Ratio (cc/g) | WT (min) | ST (min) | 1 d-CS (MPa) |
|---|---|---|---|---|---|
| | | 0.35 | — | — | ※ |
| | 0.50 | 0.28 | — | — | ※ |
| | | 0.33 | — | — | ※ |
| | | 0.35 | — | — | ※ |
| | 0.60 | 0.28 | — | — | ※ |
| | | 0.33 | — | — | ※ |
| | | 0.35 | — | — | ※ |
| | 0.75 | 0.28 | — | — | ※ |
| | | 0.33 | — | — | ※ |
| | | 0.35 | — | — | ※ |
| 65/35 | 0.25 | 0.28 | — | — | * |
| | | 0.33 | — | — | * |
| | | 0.35 | — | — | * |
| | 0.50 | 0.28 | — | — | ※ |
| | | 0.33 | — | — | ※ |
| | | 0.35 | — | — | ※ |
| | 0.60 | 0.28 | — | — | ※ |
| | | 0.33 | — | — | ※ |
| | | 0.35 | — | — | ※ |
| | 0.75 | 0.28 | — | — | ※ |
| | | 0.33 | — | — | ※ |
| | | 0.35 | — | — | ※ |

The molded lumps prepared from DCPA/CSH cement collapse and disintegrate when they are immersed in Hanks' solution (*), or their compressive strength cannot be measured after being immersed in Hanks' solution for 1 day (※) as shown in Table 3. Apparently the powder component having only DCPA and CSH phases does not give a satisfactory result.

Control 4: DCPA/CSH Cement and $NH_4H_2PO_4$ Setting Solution

TABLE 4

DCPA/CSH mixed with 0.25-0.75M $NH_4H_2PO_4$

| DCPA/CSH (weight ratio) | $NH_4H_2PO_4$ concentration (M) | L/P ratio (cc/g) | WT (min) | ST (min) | 1 d-CS (MPa) |
|---|---|---|---|---|---|
| 90/10 | 0.25 | 0.28 | — | — | ※ |
| | | 0.33 | — | — | ※ |
| | | 0.35 | — | — | ※ |
| | 0.50 | 0.28 | — | — | ※ |
| | | 0.33 | — | — | ※ |
| | | 0.35 | — | — | ※ |
| | 0.60 | 0.28 | — | — | ※ |
| | | 0.33 | — | — | ※ |
| | | 0.35 | — | — | ※ |
| | 0.75 | 0.28 | — | — | ※ |
| | | 0.33 | — | — | ※ |
| | | 0.35 | — | — | ※ |
| 75/25 | 0.25 | 0.28 | — | — | ※ |
| | | 0.33 | — | — | ※ |
| | | 0.35 | — | — | ※ |
| | 0.50 | 0.28 | — | — | ※ |
| | | 0.33 | — | — | ※ |
| | | 0.35 | — | — | ※ |
| | 0.60 | 0.28 | — | — | ※ |
| | | 0.33 | — | — | ※ |
| | | 0.35 | — | — | ※ |
| | 0.75 | 0.28 | — | — | ※ |
| | | 0.33 | — | — | ※ |
| | | 0.35 | — | — | ※ |
| 65/35 | 0.25 | 0.28 | — | — | ※ |
| | | 0.33 | — | — | ※ |
| | | 0.35 | — | — | ※ |
| | 0.50 | 0.28 | — | — | ※ |
| | | 0.33 | — | — | ※ |
| | | 0.35 | — | — | ※ |
| | 0.60 | 0.28 | — | — | ※ |
| | | 0.33 | — | — | ※ |
| | | 0.35 | — | — | ※ |
| | 0.75 | 0.28 | — | — | ※ |
| | | 0.33 | — | — | ※ |
| | | 0.35 | — | — | ※ |

The compressive strength of the molded lumps prepared from DCPA/CSH cement cannot be measured after being immersed in Hanks' solution for 1 day (※) as shown in Table 4. Apparently the powder component having only DCPA and CSH phases does not give a satisfactory result.

For Tables 5-14

| TTCP/DCPA:CSH (weight ratio) | TTCP:DCPA:CSH (weight ratio) |
|---|---|
| 90:10 | 2.69:1:0.41 |
| 85:15 | 2.69:1:0.65 |
| 80:20 | 2.69:1:0.92 |
| 75:25 | 2.69:1:1.23 |
| 65:35 | 2.69:1:1.99 |
| 55:45 | 2.69:1:3.02 |
| 45:55 | 2.69:1:4.51 |
| 35:65 | 2.69:1:6.85 |
| 25:75 | 2.69:1:11.07 |
| 10:90 | 2.69:1:33.21 |

Note:
TTCP and DCPA have a molar ratio of 1:1 under all conditions

EXAMPLE 1

(TTCP/DCPA)/CSH Cement and Various Setting Solutions

TABLE 5

75 wt % phosphate (TTCP/DCPA)/25 wt % CSH composite cement

| Setting solution | Conc. (M) | Solution pH value | WT (min) | ST (min) | 1 d-CS (MPa) |
|---|---|---|---|---|---|
| $K_2HPO_4$ | 1 | 9.27 | 1.53 ± 0.21 | 2.72 ± 0.26 | 15.35 ± 0.85 |
| (L/P = 0.33) | 0.75 | 9.20 | 1.88 ± 0.13 | 3.08 ± 0.15 | 15.46 ± 3.51 |
|  | 0.5 | 9.17 | 2.85 ± 0.13 | 3.93 ± 0.16 | 18.39 ± 1.53 |
|  | 0.25 | 9.15 | — | — | 24.12 ± 6.30 |
| $(NH_4)_2HPO_4$ | 1 | 8.17 | 4.88 ± 0.13 | 6.93 ± 0.25 | 27.77 ± 1.6 |
| (L/P = 0.33) | 0.75 | 8.09 | 5.47 ± 0.13 | 7.45 ± 0.16 | 25.37 ± 0.69 |
|  | 0.6 | 7.97 | 5.77 ± 0.13 | 7.53 ± 0.27 | 41.02 ± 3.77 |
|  | 0.5 | 7.95 | 7.85 ± 0.32 | 10.05 ± 0.33 | 21.58 ± 1.82 |
|  | 0.25 | 7.92 | 13.5 ± 0.5 | 16.28 ± 1.1 | * |
| $(NH_4)H_2PO_4$ | 1 | 3.96 | 4.95 ± 0.5 | 7.5 ± 0.5 | * |
| (L/P = 0.33) | 0.75 | 3.99 | 6.63 ± 0.38 | 8.93 ± 0.33 | * |
|  | 0.5 | 4.28 | 9.43 ± 0.416 | 12.6 ± 0.53 | * |
|  | 0.25 | 4.30 | 11.42 ± 0.5 | 15.18 ± 0.27 | * |
| $NaH_2PO_4 \cdot 2H_2O$ | 1 | 3.89 | 6.5 ± 0.43 | 9 ± 0.33 | 23.82 ± 3.23 |
| (L/P = 0.33) | 0.75 | 3.97 | 8.05 ± 0.25 | 11.05 ± 0.75 | 18.96 ± 1.79 |
|  | 0.5 | 4.13 | 10.72 ± 0.25 | 14.68 ± 0.28 | * |
|  | 0.25 | 4.22 | 12.92 ± 0.67 | 16.16 ± 1.03 | * |

It can be summarized from the data shown in Table 5 as follows:
1. $K_2HPO_4$-derived hardened cement composites have too short WT/ST and low CS.
2. $(NH_4)H_2PO_4$-derived hardened cement composites have reasonable WT/ST, but is dispersed after immersion in Hanks' solution.
3. $NaH_2PO_4 \cdot 2H_2O$-derived hardened cement composites have reasonable WT/ST, but too acidic and low strength.
4. Among all setting solutions tested, $(NH_4)_2HPO_4$ results in the highest CS.
5. Among all $(NH_4)_2HPO_4$ concentrations, 0.6M gives the highest CS (41 MPa).

EXAMPLE 2

TTCP/DCPA/CSH Mixed with 0.60M $(NH_4)_2HPO_4$

TABLE 6

TTCP/DCPA/CSH mixed with 0.60M $(NH_4)_2HPO_4$.

| TTCP/DCPA:CSH (weight ratio) | Setting solution | L/P ratio (cc/g) | 1 d-CS (MPa) | WT/ST (Min) | Cytotoxicity O.D. (%) ($Al_2O_3$ as control-100%) |
|---|---|---|---|---|---|
| 90:10 | 0.60M $(NH_4)_2HPO_4$ | 0.28 | 45.10 ± 3.50 | 6.1 ± 0.1/7.1 ± 0.1 | 86.40 ± 2.20 |
| 85:15 | 0.60M $(NH_4)_2HPO_4$ | 0.28 | 44.50 ± 5.50 | 5.8 ± 0.1/6.9 ± 0.2 | 91.76 ± 4.90 |
| 80:20 | 0.60M $(NH_4)_2HPO_4$ | 0.28 | 40.93 ± 3.98 | 6.6 ± 0.3/7.7 ± 0.3 | 89.32 ± 0.28 |
| 75:25 | 0.60M $(NH_4)_2HPO_4$ | 0.28 | 40.45 ± 2.39 | 5.8 ± 0.1/7.5 ± 0.3 | 95.49 ± 3.04 |
| 65:35 | 0.60M $(NH_4)_2HPO_4$ | 0.28 | 26.53 ± 1.57 | 5.5 ± 0.3/7.5 ± 0.4 | 84.94 ± 2.98 |
| 55:45 | 0.60M $(NH_4)_2HPO_4$ | 0.28 | 28.07 ± 1.54 | 5.2 ± 0.2/6.8 ± 0.3 | 101.99 ± 0.74 |
| 45:55 | 0.60M $(NH_4)_2HPO_4$ | 0.28 | 27.02 ± 1.29 | 5.5 ± 0.2/6.9 ± 0.1 | 89.29 ± 10.44 |
| 35:65 | 0.60M $(NH_4)_2HPO_4$ | 0.28 | 14.10 ± 3.10 | 4.4 ± 0.3/6.4 ± 0.4 | 97.31 ± 1.91 |
| 25:75 | 0.60M $(NH_4)_2HPO_4$ | 0.28 | 13.80 ± 1.61 | 5.1 ± 0.1/6.1 ± 0.4 | 85.97 ± 3.94 |
| 10:90 | 0.60M $(NH_4)_2HPO_4$ | 0.28 | 9.77 ± 1.15 | 5.0 ± 0.2/7.9 ± 0.2 | 93.17 ± 8.63 |

Summary of the results shown in Table 6 (TTCP/DCPA/CSH mixed with 0.60M $(NH_4)_2HPO_4$):
(1) When CSH contents are higher than about 65 wt % in the TTCP/DCPA/CSH cement powder, their CS values become too low (<15 MPa). The appropriate CSH content under the test conditions should be less than about 65 wt %. To obtain a higher strength (CS > 30 MPa), the CSH content should be less than about 35 wt %.
(2) All cytotoxicity values are acceptably greater than 80% for all CSH contents (from about 10 wt % to about 90 wt %) when 0.60M $(NH_4)_2HPO_4$ is used as hardening solution.

EXAMPLE 3

TTCP/DCPA/CSH Mixed with 0.20-3.0 M $(NH_4)_2HPO_4$

TABLE 7

TTCP/DCPA/CSH (TTCP/DCPA:CSH = 90:10) mixed with 0.20-3.00M $(NH_4)_2HPO_4$

| Powder | $(NH_4)_2HPO_4$ concentration (M) | L/P ratio (cc/g) | 1 d-CS (MPa) | WT/ST (Min) | Cytotoxicity O.D. (%) ($Al_2O_3$ as control-100%) |
|---|---|---|---|---|---|
| TTCP/ | 0.20 | 0.28 | * | — | — |
| DCPA:CSH | 0.25 | 0.28 | * | 8.1 ± 0.2/9.9 ± 0.2 | 104.95 ± 6.46 |
| (90:10) | 0.50 | 0.28 | 32.37 ± 3.10 | 5.9 ± 0.3/7.2 ± 0.7 | 91.31 ± 5.77 |
| | 0.60 | 0.28 | 45.11 ± 3.50 | 6.1 ± 0.2/7.1 ± 0.1 | 91.61 ± 6.06 |
| | 0.75 | 0.28 | 35.48 ± 1.8 | 5.9 ± 0.3/6.9 ± 0.2 | 86.99 ± 5.13 |
| | 1.00 | 0.28 | 35.79 ± 2.60 | 5.7 ± 0.1/6.3 ± 0.1 | 74.09 ± 3.44 |
| | 2.00 | 0.28 | 41.75 ± 2.60 | 4.5 ± 0.5/5.9 ± 0.3 | 57.85 ± 4.22 |
| | 3.00 | 0.28 | 42.68 ± 2.60 | 4.7 ± 0.2/6.0 ± 0.1 | 46.80 ± 5.04 |

Summary of the results shown in Table 7 (TTCP/DCPA/CSH (TTCP/DCPA:CSH = 90:10) mixed with 0.20-3.00M $(NH_4)_2HPO_4$):

(1) When the $(NH_4)_2HPO_4$ concentration is too low (0.25M or lower under the present test conditions), the hardened paste is dispersed upon immersion in Hanks' solution and its strength cannot be measured.

(2) Although ammonium is a critical life-sustaining element, the $(NH_4)_2HPO_4$ concentration cannot be too high (2M or higher under the present test conditions) for reducing cytotoxicity level.

(3) The appropriate $(NH_4)_2HPO_4$ concentration should be in the window of 0.25M-2.0M, preferably 0.5M-1.0M. (or the $NH_4^+$ ion concentration in the window of 0.50M-4.0M, preferably 1.0M-2.0M)

EXAMPLE 4

TTCP/DCPA/CSH Mixed with 0.20-3.0 M $(NH_4)_2HPO_4$

TABLE 8

TTCP/DCPA/CSH (TTCP/DCPA:CSH = 75:25) mixed with 0.20-3.00M $(NH_4)_2HPO_4$

| Powder | $(NH_4)_2HPO_4$ concentration (M) | L/P Ratio (cc/g) | 1 d-CS (MPa) | WT/ST (Min) | Cytotoxicity O.D. (%) ($Al_2O_3$ as control-100%) |
|---|---|---|---|---|---|
| TTCP/ | 0.20 | 0.28 | * | — | — |
| DCPA:CSH | 0.25 | 0.28 | * | 13.5 ± 0.5/16.3 ± 1.1 | 98.94 ± 3.41 |
| (75:25) | 0.50 | 0.28 | 21.58 ± 1.82 | 7.9 ± 0.3/10.1 ± 0.3 | 90.83 ± 6.02 |
| | 0.60 | 0.28 | 40.45 ± 2.39 | 5.8 ± 0.1/7.5 ± 0.3 | 88.17 ± 1.39 |
| | 0.75 | 0.28 | 25.37 ± 0.69 | 5.5 ± 0.1/7.5 ± 0.2 | 93.32 ± 5.01 |
| | 1.00 | 0.28 | 27.77 ± 1.60 | 4.9 ± 0.1/6.9 ± 0.3 | 91.21 ± 1.99 |
| | 2.00 | 0.28 | 24.53 ± 1.80 | 3.6 ± 0.5/4.8 ± 0.3 | 74.42 ± 3.25 |
| | 3.00 | 0.28 | 32.86 ± 2.10 | 2.9 ± 0.1/4.2 ± 0.3 | 59.79 ± 3.23 |

Summary of the results shown in Table 8 (TTCP/DCPA/CSH (TTCP/DCPA:CSH = 75:25) mixed with 0.20-3.00M $(NH_4)_2HPO_4$):

(1) When the $(NH_4)_2HPO_4$ concentration is too low (0.25M or lower under the present test conditions), the hardened paste is dispersed upon immersion in Hanks' solution and its strength cannot be measured.

(2) Although ammonium is a critical life-sustaining element, the $(NH_4)_2HPO_4$ concentration cannot be too high (>2M under the present test conditions) for reducing cytotoxicity level.

(3) The appropriate $(NH_4)_2HPO_4$ concentration should be in the window of 0.25M-2.0M, preferably 0.5M-1.0M. (or the $NH_4^+$ ion concentration in the window of 0.50M-4.0M, preferably 1.0M-2.0M)

EXAMPLE 5

TTCP/DCPA/CSH Mixed with 0.25-1.0 M $(NH_4)_2HPO_4$

TABLE 9

TTCP/DCPA/CSH (TTCP/DCPA:CSH = 65:35) mixed with 0.25-1.0M $(NH_4)_2HPO_4$

| Powder | $(NH_4)_2HPO_4$ concentration (M) | L/P (cc/g) | 1-d CS (MPa) |
|---|---|---|---|
| TTCP/ DCPA:CSH (65:35) | 1.00 | 0.35 | 21.24 ± 1.82 |
| | | 0.33 | 23.12 ± 1.21 |
| | | 0.30 | 23.33 ± 1.38 |
| | | 0.28 | 23.52 ± 1.67 |
| | 0.75 | 0.35 | 24.32 ± 1.56 |
| | | 0.33 | 25.62 ± 0.93 |
| | | 0.30 | 24.36 ± 1.62 |
| | | 0.28 | 29.54 ± 1.13 |
| | 0.50 | 0.35 | 18.36 ± 1.45 |
| | | 0.33 | 22.59 ± 1.61 |
| | | 0.30 | 26.75 ± 1.51 |
| | | 0.28 | 31.37 ± 0.81 |
| | 0.45 | 0.35 | 34.23 ± 0.61 |
| | | 0.33 | 30.77 ± 1.57 |
| | | 0.30 | 25.01 ± 0.56 |
| | 0.40 | 0.28 | 22.65 ± 1.23 |
| | | 0.35 | 27.32 ± 1.45 |
| | | 0.33 | 32.51 ± 0.72 |
| | | 0.30 | 28.77 ± 1.22 |
| | | 0.28 | 14.16 ± 1.15 |
| | 0.25 | 0.35 | * |
| | | 0.33 | * |
| | | 0.30 | * |
| | | 0.28 | * |

Summary of the results shown in Table 9 (TTCP/DCPA/CSH (TTCP/DCPA:CSH = 65:35) mixed with 0.25-1.0M $(NH_4)_2HPO_4$):
(1) When the $(NH_4)_2HPO_4$ concentration is too low (0.25M or lower under the present test conditions), the hardened paste is dispersed upon immersion in Hanks' solution and its strength cannot be measured.
(2) Except a few cases, all 1-d CS values are higher than 20 MPa, and, under certain conditions, higher than 30 MPa.

EXAMPLE 6

TTCP/DCPA/CSH Mixed with 0.40-1.0 M $(NH_4)_2HPO_4$

TABLE 10

TTCP/DCPA/CSH (TTCP/DCPA:CSH = 55:45) mixed with 0.40-1.00M $(NH_4)_2HPO_4$

| Powder | $(NH_4)_2HPO_4$ concentration (M) | L/P Ratio (cc/g) | WT (min) | ST (min) | 1-d CS (MPa) |
|---|---|---|---|---|---|
| TTCP/ DCPA:CSH (55:45) | 0.40 | 0.35 | 10.3 ± 0.3 | 11.9 ± 0.1 | 28.87 ± 2.52 |
| | | 0.33 | 9.3 ± 0.3 | 10.9 ± 0.2 | 30.46 ± 1.89 |
| | | 0.30 | 7.9 ± 0.5 | 9.4 ± 0.3 | 26.62 ± 2.23 |
| | | 0.28 | 6.9 ± 0.4 | 8.6 ± 0.2 | 24.96 ± 3.79 |
| | 0.45 | 0.35 | 8.9 ± 0.1 | 10.8 ± 0.2 | 27.93 ± 2.69 |
| | | 0.33 | 7.7 ± 0.3 | 9.6 ± 0.2 | 26.22 ± 2.51 |
| | | 0.30 | 6.6 ± 0.2 | 8.5 ± 0.3 | 26.71 ± 1.41 |
| | | 0.28 | 5.4 ± 0.4 | 7.4 ± 0.4 | 27.82 ± 2.59 |
| | 0.50 | 0.35 | 9.2 ± 0.1 | 11.2 ± 0.2 | 24.67 ± 2.23 |
| | | 0.33 | 8.4 ± 0.3 | 10.3 ± 0.2 | 27.86 ± 2.26 |
| | | 0.30 | 7.2 ± 0.2 | 9.2 ± 0.3 | 32.05 ± 3.02 |
| | | 0.28 | 6.0 ± 0.2 | 7.5 ± 0.3 | 34.70 ± 1.52 |
| | | 0.26 | 5.4 ± 0.2 | 7.4 ± 0.1 | 30.50 ± 3.77 |
| | 0.60 | 0.35 | 8.5 ± 0.3 | 10.3 ± 0.3 | 28.60 ± 1.99 |
| | | 0.33 | 7.3 ± 0.3 | 9.2 ± 0.2 | 27.10 ± 1.28 |
| | | 0.3 | 6.3 ± 0.1 | 8.4 ± 0.1 | 25.74 ± 2.20 |
| | | 0.28 | 5.2 ± 0.2 | 6.8 ± 0.3 | 28.07 ± 1.54 |
| | 0.75 | 0.35 | 6.4 ± 0.4 | 8.5 ± 0.2 | 23.40 ± 3.55 |
| | | 0.33 | 5.3 ± 0.3 | 7.5 ± 0.4 | 29.25 ± 1.45 |
| | | 0.30 | 5.2 ± 0.3 | 7.1 ± 0.2 | 29.59 ± 2.65 |
| | | 0.28 | 4.7 ± 0.3 | 6.5 ± 0.3 | 30.00 ± 2.83 |
| | 1.00 | 0.35 | 5.3 ± 0.1 | 7.0 ± 0.2 | 28.46 ± 3.38 |
| | | 0.33 | 4.5 ± 0.2 | 6.2 ± 0.2 | 30.71 ± 2.76 |
| | | 0.30 | 3.7 ± 0.3 | 5.3 ± 0.1 | 25.71 ± 3.86 |
| | | 0.28 | 2.9 ± 0.3 | 4.2 ± 0.3 | 29.58 ± 1.24 |

Summary of the results shown in Table 10 (TTCP/DCPA/CSH (TTCP/DCPA:CSH = 55:45) mixed with 0.40-1.00M $(NH_4)_2HPO_4$):
(1) All 1-d CS values are higher than 20 MPa, and, under certain conditions, higher than 30 MPa.
(2) For higher concentration (1.0M) and lower L/P values (lower than 0.33 cc/g), the WT/ST are a little too short.

EXAMPLE 7

TTCP/DCPA/CSH Mixed with 0.40-0.60 M $(NH_4)_2HPO_4$

TABLE 11

TTCP/DCPA/CSH (TTCP/DCPA:CSH = 45:55) mixed with 0.40-0.60M $(NH_4)_2HPO_4$

| Powder | $(NH_4)_2HPO_4$ concentration (M) | L/P Ratio (cc/g) | WT (min) | ST (min) | 1-d CS (MPa) |
|---|---|---|---|---|---|
| TTCP/ DCPA:CSH (45:55) | 0.40 | 0.35 | 8.2 ± 0.3 | 10.7 ± 0.2 | 21.1 ± 1.0 |
| | | 0.33 | 7.5 ± 0.2 | 9.6 ± 0.3 | 23.3 ± 2.0 |
| | | 0.30 | 6.1 ± 0.3 | 8.3 ± 0.2 | 27.1 ± 2.2 |
| | 0.50 | 0.35 | 7.6 ± 0.3 | 10.2 ± 0.2 | 22.3 ± 0.5 |
| | | 0.33 | 7.0 ± 0.5 | 9.1 ± 0.2 | 22.1 ± 2.2 |
| | | 0.30 | 5.8 ± 0.2 | 7.8 ± 0.1 | 24.1 ± 1.6 |
| | 0.60 | 0.35 | 7.9 ± 0.3 | 10.0 ± 0.2 | 21.4 ± 2.0 |
| | | 0.33 | 6.6 ± 0.4 | 9.0 ± 0.6 | 23.8 ± 1.7 |
| | | 0.30 | 5.5 ± 0.1 | 7.5 ± 0.2 | 23.8 ± 1.7 |

Summary of the results shown in Table 11 (TTCP/DCPA/CSH (TTCP/DCPA:CSH = 45:55) mixed with 0.40-0.60M $(NH_4)_2HPO_4$):
(1) All 1-d CS values are higher than 20 MPa
(2) Working times are longer than 5.5 min and setting times are longer than 7.5 min under all testing conditions.

TABLE 12

CS (MPa) of TTCP/DCPA/CSH after immersion in Hanks' solution for different days

| TTCP/ DCPA:CSH (weight ratio) | Setting solution | L/P ratio (cc/g) | 1 d-CS | 3 d-CS | 7 d-CS | 14 d-CS | 28 d-CS | 42 d-CS |
|---|---|---|---|---|---|---|---|---|
| 90:10 | 0.60M $(NH_4)_2HPO_4$ | 0.28 | 44.60 ± 3.64 | 40.52 ± 4.68 | 40.17 ± 3.47 | 39.86 ± 4.96 | 39.46 ± 3.17 | 37.98 ± 3.79 |
| 85:15 | 0.60M $(NH_4)_2HPO_4$ | 0.28 | 43.70 ± 4.71 | 41.56 ± 4.23 | 40.20 ± 3.62 | 38.47 ± 3.32 | 37.44 ± 4.68 | 35.24 ± 5.13 |
| 80:20 | 0.60M $(NH_4)_2HPO_4$ | 0.28 | 40.17 ± 4.76 | 37.13 ± 5.14 | 36.05 ± 3.47 | 35.76 ± 4.79 | 35.26 ± 3.46 | 34.77 ± 3.79 |
| 75:25 | 0.60M $(NH_4)_2HPO_4$ | 0.28 | 40.45 ± 2.39 | 39.25 ± 3.25 | 38.43 ± 1.87 | 38.34 ± 2.15 | 36.25 ± 1.51 | 32.54 ± 2.39 |
| 65:35 | 0.45M $(NH_4)_2HPO_4$ | 0.35 | 34.23 ± 0.60 | 33.65 ± 1.75 | 31.25 ± 1.87 | 30.82 ± 2.15 | 29.47 ± 1.66 | 27.76 ± 2.59 |
| 55:45 | 0.60M $(NH_4)_2HPO_4$ | 0.35 | 28.60 ± 2.00 | 19.58 ± 1.40 | 20.02 ± 1.77 | 14.59 ± 1.72 | 11.67 ± 1.22 | 8.09 ± 1.04 |

Summary of the results shown in Table 12:
(1) Except the "55:45" composite, all 42 d-CS values are higher than 20 MPa, indicating a mild decay in strength even after immersion in Hanks' solution for 42 days. When the CSH content is increased to 45 wt %, however, the CS value of the composite decreases very significantly.

EXAMPLE 8

Effects of Addition of Organic Acids on TTCP/DCPA/CSH Mixed with 1.0 M $(NH_4)_2HPO_4$

TABLE 13

Effects of addition of organic acids (tartaric acid, citric acid and malic acid) on properties of TTCP/DCPA/CSH (TTCP/DCPA:CSH = 75:25) mixed with 1M $(NH_4)_2HPO_4$

| Organic acid | Concentration of organic acid (M) | L/P Ratio (cc/g) | Solution pH | WT (min) | ST (min) | 1 d-CS (MPa) |
|---|---|---|---|---|---|---|
| Malic acid | 0.4 | 0.40 | 5.31 | 7.8 ± 0.2 | 9.9 ± 0.4 | 20.17 ± 2.20 |
| | 0.3 | 0.40 | 5.86 | 8.4 ± 0.4 | 10.5 ± 0.5 | 24.15 ± 2.73 |
| | 0.2 | 0.40 | 6.39 | 9.0 ± 0.5 | 10.50 ± 0.5 | 23.44 ± 3.79 |
| | 0.1 | 0.40 | 6.98 | 9.4 ± 0.4 | 10.4 ± 0.5 | 23.90 ± 3.05 |
| Citric acid | 0.4 | 0.33 | 4.71 | 2.4 ± 0.3 | 4.0 ± 0.3 | 27.65 ± 3.24 |
| | 0.3 | 0.33 | 5.28 | 4.7 ± 0.6 | 7.1 ± 0.1 | 30.08 ± 1.44 |
| | 0.2 | 0.33 | 5.94 | 7.0 ± 0.3 | 10.0 ± 0.4 | 29..48 ± 1.46 |
| | 0.1 | 0.33 | 6.71 | 9.2 ± 0.4 | 10.3 ± 0.4 | 31.66 ± 2.49 |
| Tartaric acid | 0.4 | 0.33 | 5.10 | 3.9 ± 0.3 | 6.8 ± 0.2 | 32.38 ± 2.48 |
| | 0.35 | 0.33 | 5.57 | 4.2 ± 0.2 | 7.1 ± 0.1 | 34.60 ± 3.70 |
| | 0.3 | 0.33 | 5.62 | 6.0 ± 0.5 | 9.8 ± 0.2 | 30.97 ± 2.86 |

TABLE 13-continued

Effects of addition of organic acids (tartaric acid, citric acid and malic acid) on properties of TTCP/DCPA/CSH (TTCP/DCPA:CSH = 75:25) mixed with 1M (NH$_4$)$_2$HPO$_4$

| Organic acid | Concentration of organic acid (M) | L/P Ratio (cc/g) | Solution pH | WT (min) | ST (min) | 1 d-CS (MPa) |
|---|---|---|---|---|---|---|
| | 0.2 | 0.33 | 6.25 | 7.2 ± 0.4 | 10.2 ± 0.4 | 26.04 ± 3.64 |
| | 0.1 | 0.33 | 6.99 | 9.4 ± 0.4 | 11.2 ± 0.2 | 27.36 ± 5.31 |

Summary of the results shown in Table 13:
(1) Addition of malic acid 1M (NH$_4$)$_2$HPO$_4$ setting solution decreases the CS value of the hardened composite cement
(2) Addition of citric acid 1M (NH$_4$)$_2$HPO$_4$ setting solution increases the CS value of the hardened composite cement (from about 28 MPa to about 32 MPa)
(3) Addition of tartaric acid 1M (NH$_4$)$_2$HPO$_4$ setting solution increases the CS value of the hardened composite cement (from about 28 MPa to about 35 MPa)

Preparation of a TTCP/DCPA/CSH Composite Dense Block

Appropriate amounts of TTCP and DCPA powders were uniformly mixed in a ball miller, followed by uniformly mixing with appropriate amount of CSH powder. The resultant TTCP/DCPA/CSH mixed powders were mixed uniformly with a desirable setting solution (e.g., 0.6M (NH$_4$)$_2$HPO$_4$) at a desirable L/P ratio (e.g., 0.28 cc/g) to form a TTCP/DCPA/CSH paste.

Prior to being fully hardened, the paste was placed in a mold under a desirable pressure (at a maximum pressure of 150, 300 or 450 Kgf) to squeeze a portion of the liquid out of the paste. After being removed from the mold, one group of the hardened composite samples were placed in a moisture-proof container for 1 day. Another group of samples were further impregnated in an impregnation solution (1M (NH$_4$)$_2$HPO$_4$ or 1M K$_2$HPO$_4$) at a desirable temperature (37° C.) for 1 day, followed by drying in an oven at 50° C. for 1 day.

Preparation of TTCP/DCPA/CSH Composite Porous Blocks

Appropriate amounts of TTCP and DCPA powders were uniformly mixed in a ball miller, followed by uniformly mixing with appropriate amount of CSH powder. The resultant TTCP/DCPA/CSH mixed powders were mixed uniformly with a desirable setting solution (e.g., 0.6M (NH$_4$)$_2$HPO$_4$) at a desirable L/P ratio (e.g., 0.28 cc/g) to form a TTCP/DCPA/CSH paste.

The composite paste was then uniformly mixed with a pore-forming agent (e.g. KCl particles) with a desirable weight ratio (e.g. TTCP/DCPA/CSH:KCl=1:1 or 1:2) to form a TTCP/DCPA/CSH/KCl paste.

Prior to being fully hardened, the composite paste was placed in a mold under a desirable pressure (at a maximum pressure of 450 Kgf) to squeeze a portion of the liquid out of the paste. After being removed from the mold, one group of the hardened composite blocks were immersed in de-ionized water at 37° C. for 3 days to allow KCl particles to dissolve, forming a porous composite block, followed by drying in an oven at 50° C. for 1 day. Another group of samples were further impregnated in an impregnation solution (e.g. 1M (NH$_4$)$_2$HPO$_4$ or 1M K$_2$HPO$_4$) at a desirable temperature (37° C.) for 1 day to allow the strength of the porous block to increase, followed by drying in an oven at 50° C. for 1 day. To remove the residual impregnation solution from inside the pores, the impregnated porous samples were further rinsed in de-ionized water at 37° C. for 3 days.

Measurement of Porosity

The porosity of the various samples was measured according to ASTM C830-00 (2006) method, "Standard Test Methods for Apparent Porosity, Liquid Absorption, Apparent Specific Gravity, and Bulk Density of Refractory Shapes by Vacuum Pressure".

EXAMPLE 9

Dense Block

TABLE 14

Compressive strengths (MPa) of TTCP/DCPA/CSH composite dense blocks prepared from TTCP/DCPA/CSH mixed powders mixed with 0.6M (NH$_4$)$_2$HPO$_4$ (L/P = 0.28 cc/g)

| TTCP/DCPA:CSH (weight ratio) | Without impregnation treatment Molding pressure (kgf) | | | Impregnated in 1M (NH$_4$)$_2$HPO$_4$, at 37° C. for 1 d Molding pressure (kgf) | | |
|---|---|---|---|---|---|---|
| | 150 | 300 | 450 | 150 | 300 | 450 |
| 90:10 | 42.74 ± 3.20 | 49.21 ± 3.17 | 55.86 ± 1.67 | 101.38 ± 9.23 | 130.83 ± 6.88 | 167.02 ± 7.57 |
| 85:15 | 38.11 ± 2.51 | 49.21 ± 3.69 | 53.55 ± 1.14 | 100.26 ± 7.06 | 127.49 ± 11.21 | 162.95 ± 6.26 |
| 75:25 | 38.02 ± 3.00 | 46.34 ± 1.79 | 54.78 ± 7.45 | 103.07 ± 6.55 | 121.68 ± 5.07 | 137.99 ± 9.58 |
| 65:35 | 36.14 ± 1.64 | 46.32 ± 8.16 | 60.64 ± 2.34 | 101.04 ± 4.77 | 120.53 ± 7.98 | 134.78 ± 9.74 |
| 55:45 | 35.59 ± 1.32 | 48.71 ± 2.80 | 54.95 ± 4.70 | 95.14 ± 6.06 | 121.91 ± 7.68 | 128.63 ± 6.92 |

| TTCP/DCPA:CSH (weight ratio) | Impregnated in 1M K$_2$HPO$_4$, at 37° C. for 1 d Molding pressure (kgf) | | |
|---|---|---|---|
| | 150 | 300 | 450 |
| 90:10 | 111.07 ± 6.93 | 162.96 ± 8.07 | 160.07 ± 4.13 |
| 85:15 | 105.78 ± 6.81 | 142.01 ± 8.92 | 150.07 ± 3.25 |

TABLE 14-continued

Compressive strengths (MPa) of TTCP/DCPA/CSH composite dense blocks prepared
from TTCP/DCPA/CSH mixed powders mixed with 0.6M $(NH_4)_2HPO_4$ (L/P = 0.28 cc/g)

| | | | |
|---|---|---|---|
| 75:25 | 105.32 ± 7.02 | 129.10 ± 9.81 | 144.90 ± 11.33 |
| 65:35 | 98.26 ± 10.71 | 131.78 ± 6.77 | 136.85 ± 8.47 |
| 55:45 | 90.18 ± 3.63 | 132.57 ± 5.28 | 140.37 ± 3.45 |

Summary of the results shown in Table 14 (Compressive strengths of TTCP/DCPA/CSH composite dense blocks):
(1) Impregnation-treated samples have significantly higher CS values under all conditions
(2) CS values significantly increase with higher molding pressure under all conditions

EXAMPLE 10

Porous Block

TABLE 15

Porosity values (vol %) of TTCP/DCPA/CSH composite porous blocks
prepared from TTCP/DCPA/CSH/KCl (pore-forming agent)-mixed
powders mixed with 0.6M $(NH_4)_2HPO_4$ (L/P = 0.33 cc/g)

| TTCP/DCPA:CSH (weight ratio) | TTCP/DCPA/CSH:KCl = 1:1 (weight ratio) | TTCP/DCPA/CSH:KCl = 1:2 (weight ratio) |
|---|---|---|
| 90:10 | 46.02 ± 2.87 | 81.51 ± 6.57 |
| 85:15 | 57.66 ± 0.98 | 83.77 ± 5.61 |
| 75:25 | 59.82 ± 1.16 | 84.32 ± 6.71 |
| 65:35 | 63.02 ± 1.41 | 87.86 ± 3.74 |
| 55:45 | 59.98 ± 0.87 | 88.69 ± 5.72 |

Summary of the results shown in Table 15 (TTCP/DCPA/CSH composite porous blocks prepared from TTCP/DCPA/CSH/KCl (pore-forming agent)-mixed powders mixed with 0.6M $(NH_4)_2HPO_4$):
(1) The porosity values are in the range 46-63% at TTCP/DCPA/CSH:KCl = 1:1, and 81-89% at TTCP/DCPA/CSH:KCl = 1:2, which are ideal for use as a tissue-engineered scaffold.
(2) The porosity value generally increases with increasing CSH content in the composite.

EXAMPLE 11

Animal Study and Measurement of Composite Implant Resorption Ratios

Animal study was performed at National Cheng-Kung University Medical College Animal Center, Tainan, Taiwan. Adult (weighing 2.8-3.5 kg), healthy, male New Zealand white rabbits were used as experimental animals. The rabbits were housed individually in stainless steel cages which had free access to food and water. An acclimation period of a minimum of 7 days was allowed between receipt of the animals and the start of the study. Injection sites were shaved and cleansed with 70% ethanol and Betadine™ (povidone iodine 10%). All animals were operated under general anesthesia. Pentobarbital sodium (0.1 ml/100 g, Tokyo Kasei Kogyo, Tokyo, Japan) was used as general anesthesia, while xylocalne (Fujisawa Pharmaceutical CO., Tokyo, Japan) was used as local anesthesia. To implant cement paste in the medial condyle of femur, a longitudinal incision was made on the anterior surface of the femur. The inner side of knee joint of the rabbit was cut to expose the femur. After exposure of the

TABLE 16

Compressive strength (MPa) values of TTCP/DCPA/CSH composite porous
blocks prepared from TTCP/DCPA/CSH/KCl (pore-forming agent)-mixed powders mixed with
0.6M $(NH_4)_2HPO_4$ (L/P = 0.33 cc/g)

| TTCP/DCPA:CSH (weight ratio) | Without impregnation TTCP/DCPA/CSH:KCl = 1:1 (weight ratio) | Without impregnation TTCP/DCPA/CSH:KCl = 1:2 (weight ratio) | Impregnated in 1M $(NH_4)_2HPO_4$, at 37° C. for 1 d TTCP/DCPA/CSH:KCl = 1:1 (weight ratio) | Impregnated in 1M $(NH_4)_2HPO_4$, at 37° C. for 1 d TTCP/DCPA/CSH:KCl = 1:2 (weight ratio) |
|---|---|---|---|---|
| 90:10 | 4.86 ± 0.43 | 0.92 ± 0.18 | 8.43 ± 0.73 | 1.62 ± 0.28 |
| 85:15 | 5.00 ± 0.64 | 0.82 ± 0.23 | 7.29 ± 0.54 | 1.22 ± 0.19 |
| 75:25 | 4.18 ± 0.49 | 0.74 ± 0.10 | 7.03 ± 0.49 | 0.98 ± 0.18 |
| 65:35 | 3.74 ± 0.42 | 0.51 ± 0.07 | 5.19 ± 0.26 | 0.91 ± 0.05 |
| 55:45 | 2.36 ± 0.19 | 0.42 ± 0.06 | 4.01 ± 0.56 | 0.71 ± 0.10 |

| | TTCP/DCPA:CSH (weight ratio) | Impregnated in 1M $K_2HPO_4$, at 37° C. for 1 d TTCP/DCPA/CSH:KCl = 1:1 (weight ratio) | Impregnated in 1M $K_2HPO_4$, at 37° C. for 1 d TTCP/DCPA/CSH:KCl = 1:2 (weight ratio) |
|---|---|---|---|
| | 90:10 | 8.71 ± 0.93 | 1.50 ± 0.30 |
| | 85:15 | 7.37 ± 0.98 | 1.36 ± 0.19 |
| | 75:25 | 7.40 ± 0.73 | 0.93 ± 0.23 |
| | 65:35 | 5.15 ± 0.70 | 0.87 ± 0.09 |
| | 55:45 | 4.55 ± 0.33 | 0.64 ± 0.07 |

Summary of the results shown in Table 16 (TTCP/DCPA/CSH composite porous blocks prepared from TTCP/DCPA/CSH/KCl (pore-forming agent)-mixed powders mixed with 0.6M $(NH_4)_2HPO_4$):
(1) The CS strength of the porous blocks decreases with increasing CSH content in the composite under all test conditions.
(2) The CS values of the porous blocks (w/o impregnation treatment) prepared from TTCP/DCPA/CSH/KCl are in the range about 2-5 MPa at TTCP/DCPA/CSH:KCl = 1:1, and about 0.4-0.9 MPa at TTCP/DCPA/CSH:KCl = 1:2.
(3) The impregnation treatment significantly enhances the strength of the porous blocks. The CS values of $(NH_4)_2HPO_4$-impregnated porous blocks significantly increase to 4.8-8.9 MPa at TTCP/DCPA/CSH:KCl = 1:1, and about 0.5-1.2 MPa at TTCP/DCPA/CSH:KCl = 1:2. The CS values of $K_2HPO_4$-impregnated porous blocks significantly increase to 4.8-8.8 MPa at TTCP/DCPA/CSH:KCl = 1:1, and about 0.5-1.2 MPa at TTCP/DCPA/CSH:KCl = 1:2.

femur, the periosteum was reflected and a 2 mm pilot hole was drilled. The hole was gradually widened with drills of increasing size until a final diameter of 5 mm was reached. A special 5 mm diameter drill burr was used and a ring was inserted at a depth of 10 mm to ensure appropriate length (10 mm) of the drill hole.

Two kinds of calcium phosphate/calcium sulfate composite cement paste (90 wt % TTCP/DCPA: 10 wt % CSH and 55 wt % TTCP/DCPA: 45 wt % CSH) were implanted in the prepared bone cavity. After filling of the paste, subcutaneous tissues and skin were closed up layer by layer with silk threads. To reduce the risk of peri-operative infection, the rabbits were treated with antibiotics injection subcutaneously at a dose of 40 mg/kg. The animals were sacrificed after 12 week post-operation.

After the animals were sacrificed, the femur portions were excised immediately and excess tissue was removed. Photographs of the slices by a single-lens reflex camera and an image analysis system was used to calculate the areas of residual implant. The implant resorption ratios were determined by the equation, implant resorption ratio=(cross-sectional area of original implant−cross-sectional area of residual implant)/cross-sectional area of original implant.

Summary

The average residual implant ratios for "90/10" and "55/45" samples are 81.1% (resorption ratio: 18.9%) and 67.7% (resorption ratio: 32.3%), respectively, as shown in the photographs mentioned above. That means the healing speed for the 55/45 implant is about 70% faster than for the 90/10 implant.

The invention claimed is:

1. A bone cement composition comprising a powder component and a setting liquid component with a liquid to powder ratio of 0.20 cc/g to 0.50 cc/g, wherein the powder component comprises a calcium sulfate source and a calcium phosphate source with a weight ratio of the calcium sulfate source less than 65%, based on the total weight of the calcium sulfate source and the calcium phosphate source, and the setting liquid component comprises ammonium ion ($NH_4^+$) in a concentration of about 0.5 M to 4 M, wherein the calcium phosphate source comprises tetracalcium phosphate (TTCP) and dicalcium phosphate in a molar ratio of TTCP to dicalcium phosphate of about 0.5 to about 2.5, and the calcium sulfate source is calcium sulfate hemihydrate (CSH), calcium sulfate dehydrate (CSD), or anhydrous calcium sulfate.

2. The composition of claim 1, wherein the dicalcium phosphate is dicalcium phosphate anhydrous (DCPA).

3. The composition of claim 1, wherein the calcium sulfate source of the powder component is greater than 5%, and more is of 10% to 55%, based on the total weight of the calcium sulfate source and the calcium phosphate source powder.

4. The composition of claim 1, wherein the setting liquid component comprises ammonium ion ($NH_4^+$) in a concentration of about 1.0 M to 2.0M.

5. The composition of claim 4, wherein the setting liquid component is a solution of $NH_4H_2PO_4$, $(NH_4)_2HPO_4$, $(NH_4)_3PO_4 \cdot 3H_2O$ or mixtures thereof.

6. The composition of claim 5, wherein the setting liquid component is an aqueous solution of $(NH_4)_2HPO_4$.

7. The composition of claim 6, wherein the setting liquid component further comprises citric acid or tartaric acid dissolved therein.

8. The composition of claim 7, wherein the setting liquid component has a pH of about 7.0 to about 9.0.

9. The composition of claim 1 further comprising a pore-forming agent which is to be dissolved in a solution when a hardened bone cement composite prepared therefrom is immersed in the solution.

10. The composition of claim 9, wherein the pore-forming agent is selected from the group consisting of LiCl, KCl, NaCl, $MgCl_2$, $CaCl_2$, $NaIO_3$, KI, $Na_3PO_4$, $K_3PO_4$, $Na_2CO_3$, amino acid-sodium salt, amino acid-potassium salt, glucose, polysaccharide, fatty acid-sodium salt, fatty acid-potassium salt, potassium bitartrate ($KHC_4H_4O_6$), potassium carbonate, potassium gluconate ($KC_6H_{11}O_7$), potassium-sodium tartrate ($KNaC_4H_4O_6 \cdot 4H_2O$), potassium sulfate ($K_2SO_4$), sodium sulfate, sodium lactate and mannitol.

11. The composition of claim 2, wherein the calcium phosphate source is composed of TTCP and DCPA.

12. The composition of claim 1 further comprising living cells, a growth factor or a drug in the powder component or in the setting liquid component.

13. A bone cement composition comprising a powder component and a setting liquid component with a liquid to powder ratio of 0.25 cc/g to 0.35 cc/g, wherein the powder component comprises a calcium sulfate source and a calcium phosphate source with a weight ratio of the calcium sulfate source less than 65%, based on the total weight of the calcium sulfate source and the calcium phosphate source, and the setting liquid component comprises ammonium ion ($NH_4^+$) in a concentration of about 0.5 M to 4 M, wherein the calcium phosphate source comprises tetracalcium phosphate (TTCP) and dicalcium phosphate in a molar ratio of TTCP to dicalcium phosphate of about 1, and the calcium sulfate source is calcium sulfate hemihydrate (CSH).

14. A process for preparing a hardened bone cement composite comprising forming a bone cement paste by mixing the powder component and the setting liquid component of the bone cement composition set forth in claim 1, and placing the paste at an environment to become set.

15. The process of claim 14, wherein said placing the paste at an environment to become set comprises shaping the paste in a mold, and removing the mold to form a block of hardened bone cement composite.

16. The process of claim 15 further comprising pressurizing said paste in said mold before said paste becomes set to remove a portion of liquid from said paste, so that a liquid to powder ratio of said paste decreases.

17. The process of claim 16, wherein the pressure applied to the paste in the mold is form about 1MPa to 500 MPa, preferably from 100 MPa to 500 MPa.

18. The process of claim 15 further comprising impregnating the block with an impregnating liquid for a period of time, so that a compressive strength of the resulting impregnated block removed from the impregnating liquid is increased compared to that of said block without said impregnating treatment.

19. The process of claim 18 wherein the impregnating liquid is a phosphate-containing solution.

20. The process of claim 19, wherein the phosphate-containing solution is an aqueous solution of $(NH_4)_3PO_4$, $(NH_4)_2HPO_4$, $NH_4H_2PO_4$, $K_3PO_4$, $K_2HPO_4$, $KH_2PO_4$, $Na_3PO_4$, $Na_2HPO_4$, $NaH_2PO_4$, or $H_3PO_4$.

21. The process of claim 19, wherein said phosphate-containing solution has a phosphate concentration from about 0.1 M to about 6 M, preferably from about 1 M to about 3 M.

22. The process of claim 15, wherein the powder component of the bone cement composition contains a pore-forming agent, or a pore-forming agent is added during the mixing or is mixed with the paste before shaping the paste in a mold, and said process further comprises immersing said block of hardened bone cement composite in an immersing liquid to dissolve said pore-forming agent in the immersing liquid, creating pores therein, so that a porous block is formed.

23. The process of claim 22, wherein the pore forming agent is selected from the group consisting of LiCl, KCl, NaCl, $MgCl_2$, $CaCl_2$, $NaIO_3$, KI, $Na_3PO_4$, $K_3PO_4$, $Na_2CO_3$, amino acid-sodium salt, amino acid-potassium salt, glucose, polysaccharide, fatty acid-sodium salt, fatty acid-potassium salt, potassium bitartrate ($KHC_4H_4O_6$), potassium carbonate, potassium gluconate ($KC_6H_{11}O_7$), potassium-sodium tartrate ($KNaC_4H_4O_6 \cdot 4H_2O$), potassium sulfate ($K_2SO_4$), sodium sulfate, sodium lactate and mannitol.

24. The process of claim 22, wherein the immersing liquid is an acidic aqueous solution, a basic aqueous solution, a physiological solution, an organic solvent, or water.

25. The process of claim 24, wherein the immersing liquid is a phosphate-containing solution having a phosphate concentration from about 0.1 M to about 6 M.

26. The process of claim 25, wherein the phosphate-containing solution is an aqueous solution of $(NH_4)_3PO_4$, $(NH_4)_2HPO_4$, $NH_4H_2PO_4$, $K_3PO_4$, $K_2HPO_4$, $KH_2PO_4$, $Na_3PO_4$, $Na_2HPO_4$, $NaH_2PO_4$, or $H_3PO_4$.

27. The process of claim 25, wherein said immersing liquid is water.

28. The process of claim 22 further comprising impregnating the porous block with an impregnating liquid for a period of time, so that a compressive strength of the resulting impregnated porous block removed from the impregnating liquid is increased compared to that of said porous block without said impregnating treatment.

29. The process of claim 28 wherein the impregnating liquid is a phosphate-containing solution.

30. The process of claim 29, wherein the phosphate-containing solution is an aqueous solution of $(Nh_4)_3PO_4$, $(NH_4)_2HPO_4$, $NH_4H_2PO_4$, $K_3PO_4$, $K_2HPO_4$, $KH_2PO_4$, $Na_3PO_4$, $Na_2HPO_4$, $NaH_2PO_4$, or $H_3PO_4$.

31. The process of claim 29, wherein said phosphate-containing solution has a phosphate concentration from about 0.1 to about 6 M.

32. The process of claim 24 further comprising impregnating the porous block in a suspension of living cells or a solution of growth factor or drug to deposit the living cells, the growth factor or drug onto the porous block.

33. The process of claim 22, wherein the porous block has a porosity of 50-90 vol %.

34. The process of claim 14, wherein placing the paste at an environment to become set comprises filling a hole or cavity in a bone with the paste which becomes a hardened bone cement composite in-situ.

35. A method for treating a subject comprising forming a bone cement paste by mixing the powder component and the setting liquid component of the bone cement composition set forth in claim 1 and filling a hole or cavity in a bone with said bone cement paste which set hard in the hole or cavity in need of said treatment.

36. The method of claim 35 wherein said treatment is an orthopedic treatment or a dental treatment.

37. A method for treating a subject comprising forming a bone cement paste by mixing the powder component and the setting liquid component of the bone cement composition set forth in claim 1; forming a hardened bone cement composite from said paste; and implanting said hardened bone cement composite in said subject in need of said treatment.

38. The method of claim 37 wherein said treatment is an orthopedic treatment or a dental treatment, and said hardened bone cement composite is implanted in a bone of said subject.

39. The method of claim 37 wherein said implanting comprises breaking up said hardened bone cement composite into pellets and filling a hole or cavity in a bone of said subject with said pellets.

40. The method of claim 37 further comprising mixing a pore-forming agent with the powder component or with the paste, wherein said formation of the hardened bone cement composite comprises shaping the paste in a mold; removing the mold to form a block of hardened bone cement composite with the pore-forming agent embedded therein; and immersing said block of hardened bone cement composite with the pore-forming agent embedded therein in an immersing liquid to dissolve said pore-forming agent in the immersing liquid, creating pores therein, so that a porous block is formed, and thus said implanting comprises implanting said porous block in said subject in need of said treatment.

41. The method of claim 40, wherein said implanting comprises breaking up the porous block into pellets and filling a hole or cavity in a bone of said subject with said pellets.

42. The process of claim 24, wherein the immersing liquid is a phosphate-containing solution having a phosphate concentration from about 1 M to about 3 M.

43. The process of claim 29, wherein said phosphate-containing solution has a phosphate concentration from about 1 M to about 3 M.

44. The process of claim 19, wherein said phosphate-containing solution has a phosphate concentration from about 1 M to about 3 M.

* * * * *